United States Patent
Kato (10) Patent No.: US 9,158,103 B2
(45) Date of Patent: Oct. 13, 2015

(54) ENDOSCOPE HAVING ADHESIVES WITH DIFFERENT BONDING STRENGTHS

(71) Applicant: OLYMPUS CORPORATION, Tokyo (JP)

(72) Inventor: Takahiko Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 335 days.

(21) Appl. No.: 13/759,125

(22) Filed: Feb. 5, 2013

(65) Prior Publication Data

US 2014/0043454 A1    Feb. 13, 2014

(30) Foreign Application Priority Data

Aug. 7, 2012   (JP) .................................. 2012-175243

(51) Int. Cl.
| | | |
|---|---|---|
| H04N 7/18 | (2006.01) | |
| G02B 23/24 | (2006.01) | |
| A61B 1/00 | (2006.01) | |
| A61B 1/05 | (2006.01) | |

(52) U.S. Cl.
CPC ........ *G02B 23/2469* (2013.01); *A61B 1/00163* (2013.01); *A61B 1/051* (2013.01)

(58) Field of Classification Search
CPC ........... A61B 1/00163; A61B 1/00096; A61B 1/0055; A61B 1/0064; A61B 1/0011; H04N 7/183; H04N 2005/2255
USPC ............... 348/65, 68; 600/133, 139, 141, 920
See application file for complete search history.

(56) References Cited

U.S. PATENT DOCUMENTS

| | | | |
|---|---|---|---|
| 4,677,471 A | | 6/1987 | Takamura et al. |
| 5,443,057 A | * | 8/1995 | Elmore .......................... 600/133 |
| 6,146,326 A | * | 11/2000 | Pollack et al. ................. 600/141 |
| 6,565,505 B2 | * | 5/2003 | Ishibiki .......................... 600/133 |
| 7,699,773 B2 | * | 4/2010 | Forkey et al. .................. 600/172 |

(Continued)

FOREIGN PATENT DOCUMENTS

| | | |
|---|---|---|
| EP | 0 212 426 A2 | 3/1987 |
| EP | 2 022 389 A1 | 2/2009 |

(Continued)

OTHER PUBLICATIONS

European Search Report dated Apr. 26, 2013 from corresponding European Patent Application No. 13 15 5759.7.

*Primary Examiner* — Victor Kostak
(74) *Attorney, Agent, or Firm* — Scully, Scott, Murphy & Presser, PC (57) ABSTRACT

An endoscope includes: an objective optical section including a first barrel; an image pickup optical section including a solid image pickup device, an optical member forming an optical image through the objective optical section on an image pickup surface of the solid image pickup device, and a second barrel housing the optical member and the solid image pickup device, the second barrel fixed to the first barrel after positional adjustment in an axial direction relative to the first barrel; a holding member formed of material having a linear expansion coefficient lower than linear expansion coefficients of the first and second barrels, and fixed to outer surfaces of the first and second barrels; a first adhesive that bonds the first barrel and the second barrel; and a second adhesive having a bonding strength higher than that of the first adhesive, which bonds the holding member to the first and second barrels.

11 Claims, 6 Drawing Sheets

(56) References Cited

U.S. PATENT DOCUMENTS

| | | | |
|---|---|---|---|
| 7,878,972 B2* | 2/2011 | D'Amelio et al. | 600/172 |
| 8,206,286 B2* | 6/2012 | Sato | 600/139 |
| 8,262,562 B2* | 9/2012 | Takada | 600/139 |
| 8,692,874 B2* | 4/2014 | Adler et al. | 348/65 |
| 2006/0025655 A1* | 2/2006 | Uram | 600/133 |
| 2009/0062616 A1* | 3/2009 | Nagamizu et al. | 600/173 |
| 2010/0022841 A1* | 1/2010 | Takahashi et al. | 600/162 |

FOREIGN PATENT DOCUMENTS

| | | |
|---|---|---|
| EP | 2 147 629 A2 | 1/2010 |
| JP | 2006-267166 | 10/2006 |

* cited by examiner

ENDOSCOPE HAVING ADHESIVES WITH DIFFERENT BONDING STRENGTHS

CROSS REFERENCE TO RELATED APPLICATION

This application claims benefit of Japanese Application No. 2012-175243 filed in Japan on Aug. 7, 2012, the contents of which are incorporated by this reference.

BACKGROUND OF THE INVENTION

1. Field of the Invention

The present invention relates to an endoscope that includes a first barrel and a second barrel in an image pickup optical system.

2. Description of the Related Art

Conventionally, endoscopes are used in, e.g., an industrial field and a medical field. With an endoscope, observation is performed by inserting an elongated insertion portion into, e.g., a structure or a living body. In general, in a distal end portion included in an insertion portion, an illumination optical system and an image pickup optical system included in an observation optical section are incorporated. The illumination optical system illuminates an inside of the structure or an inside of the living body. The image pickup optical system shoots an image of the inside of the structure or the inside of the living body illuminated by the illumination optical system.

The image pickup optical system includes, for example, an objective optical section and an image pickup optical section, and after focusing adjustment, the objective optical section and the image pickup optical section are integrally fixed. More specifically, the objective optical section includes a plurality of optical lenses and a first barrel, which is a lens barrel.

In the first barrel, the plurality of optical lenses is housed and fixed. The image pickup optical section includes a solid image pickup device, such as a CCD or a C-MOS sensor, and a second barrel, which is a device barrel. In the second barrel, the solid image pickup device is housed and fixed. Then, the lens barrel in the objective optical section and the device barrel in the image pickup optical section are fitted together. Then, focusing is performed by adjusting positions in an axial direction of the lens barrel and the device barrel. After completion of the focusing, the lens barrel and the device barrel are integrally fixed to form the image pickup optical system.

For example, Japanese Patent Application Laid-Open Publication No. 2006-267166 discloses an objective section of an endoscope. In the objective section of the endoscope, two objective barrels that incorporate objective members for forming an optical image of an object (corresponding to barrels in the present invention) can be bonded and adhered to each other in an air-tight manner without a decrease in optical performance. In Japanese Patent Application Laid-Open Publication No. 2006-267166, a covering that covers the entire outer circumferential faces of boundary portions of the two objective barrels with no space is provided in such a manner that the covering extends across both of the outer circumferential faces of the two objective barrels, and then, the two objective barrels and the covering are adhered to each other in an air-tight manner via brazing, soldering or welding.

SUMMARY OF THE INVENTION

An endoscope according to an aspect of the present invention includes: an objective optical section including a plurality of optical lenses, and a first barrel that houses the optical lenses, the optical lenses being integrally and fixedly provided therein; an image pickup optical section including a solid image pickup device, an optical member that forms an optical image passed through the objective optical section on an image pickup surface of the solid image pickup device, and a second barrel that houses the optical member and the solid image pickup device, the optical member and the solid image pickup device being integrally and fixedly provided therein, the second barrel being arranged so as to fit with the first barrel, and being fixed to the first barrel in an integrated manner via bonding after adjustment in position in an axial direction relative to the first barrel; a holding member including a material having a linear expansion coefficient lower than a linear expansion coefficient of the first barrel and a linear expansion coefficient of the second barrel, the holding member being fixed to a predetermined position on an outer surface of the first barrel and a predetermined position on an outer surface of the second barrel via bonding; a first adhesive that bonds the first barrel and the second barrel to each other; and a second adhesive having a bonding strength higher than the bonding strength of the first adhesive, the second adhesive bonding the holding member to the outer surface of the first barrel and the outer surface of the second barrel.

The above and other objects, features and advantages of the invention will become more clearly understood from the following description referring to the accompanying drawings.

BRIEF DESCRIPTION OF THE DRAWINGS

FIG. 5 and FIG. 6 are diagrams illustrating a different assembling procedure and FIG. 5 is a perspective view illustrating a set of a first barrel and a second barrel;

DETAILED DESCRIPTION OF THE PREFERRED EMBODIMENTS

Embodiments of the present invention will be described below with reference to the drawings.

Figure 1:
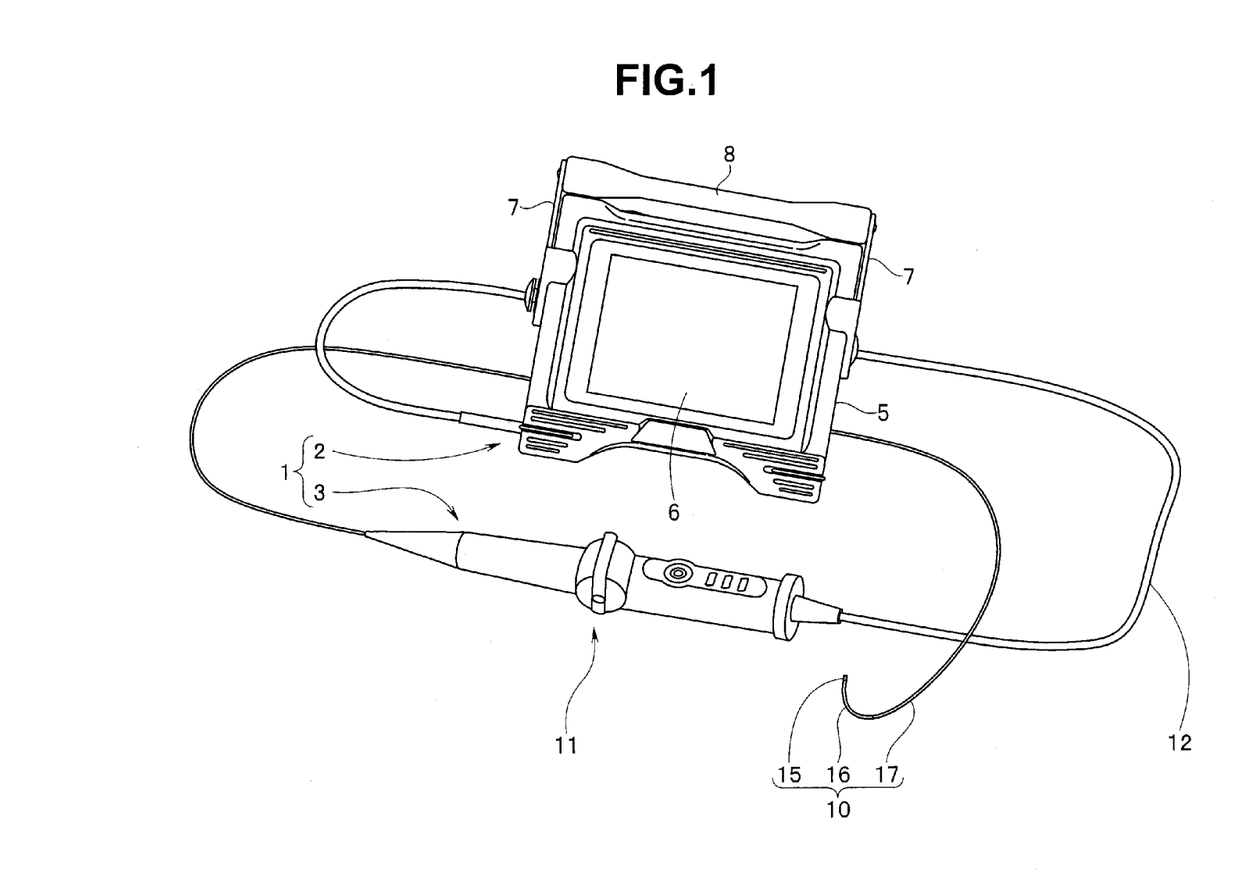
FIG. 1 is a diagram illustrating an example configuration of an endoscope apparatus including an endoscope.

In FIG. 1, reference numeral 1 denotes an endoscope apparatus. The endoscope apparatus 1 includes an endoscope body 2 and an endoscope 3. The endoscope body 2 can freely be carried. The endoscope 3 is connected to the endoscope body 2.

The endoscope body 2 includes a substantially-box shaped sheathing chassis 5. At a front face of the sheathing chassis 5, a display section 6 such as a liquid-crystal display (LCD) panel is disposed. On the display section 6, e.g., an endoscopic image and an operation menu are displayed. One end of a left carriage arm 7 and one end of a right carriage arm 7, the left and right carriage arms 7 being paired, are pivotally connected to left and right sides of the sheathing chassis 5 across the display section 6, respectively. One end of the handle portion 8 is joined to the other end side of the carriage arm 7 connected to the right side of the sheathing chassis 5, and the other end of the handle portion 8 is joined to the carriage arm 7 connected to the left side of the sheathing chassis 5.

In the present embodiment, the sheathing chassis 5 incorporates, e.g., a CPU for image processing, various types of electric components, a light source section, a battery unit, which is a power supply section (none of them illustrated). The light source section includes a light emitting device, for example, an LED.

The endoscope 3 mainly includes an insertion portion 10 and an operation portion 11. The operation portion 11 of the endoscope 3 and the endoscope body 2 are connected via a universal cable 12. In the present embodiment, the universal cable 12 extends out from the operation portion 11.

The insertion portion 10 includes a distal end portion 15, a bending portion 16 and a flexible tube portion 17 in this order from the distal end side. The bending portion 16 is disposed on the proximal end side of the distal end portion 15 and is bendable in two directions, upward and downward, or in four directions, upward, downward, leftward or rightward. The flexible tube portion 17 is disposed on the proximal end side of the bending portion 16 and is connected to the distal end side of the operation portion 11.

Figure 2:
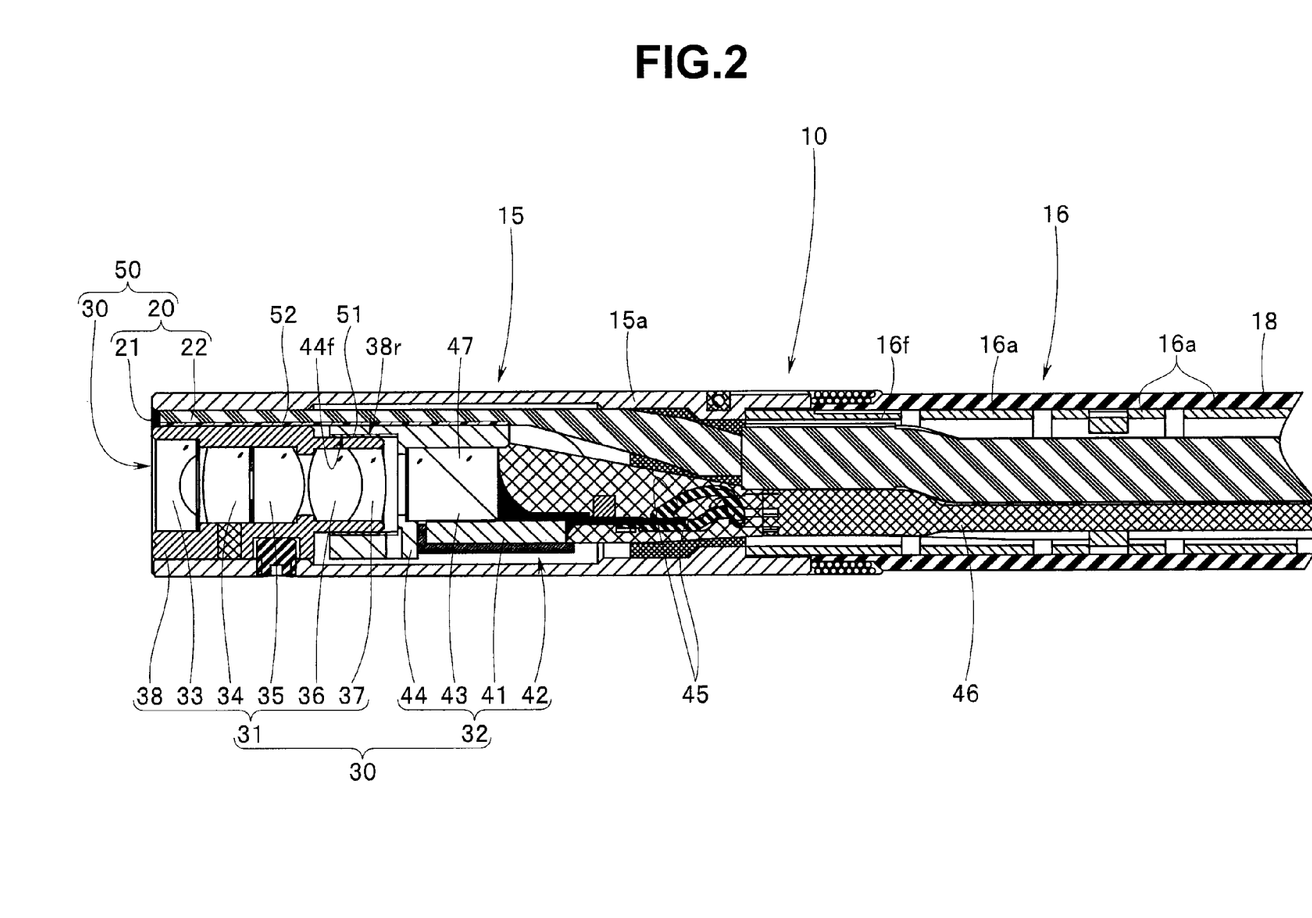
FIG. 2 is a longitudinal cross-sectional view of a configuration of a distal end portion of an endoscope including a light guide fiber bundle as an illumination optical system.

As illustrated in FIG. 2, a distal end forming member 15a included in the distal end portion 15 of the insertion portion 10 is provided with an illumination optical system 20 and an image pickup optical system 30 included in an observation optical section 50.

The illumination optical system 20 includes an illuminating light emitting section 21 and a light guide fiber bundle (hereinafter abbreviated as "light guide") 22.

The illuminating light emitting section 21 is provided at a distal end face of the distal end portion 15 so as to have a predetermined shape. The illuminating light emitting section 21 is one obtained by forming a transparent material such as optical glass into a plate shape or a lens shape.

The light guide 22 is a holding member, which will be described later. The light guide 22 illustrated in FIGS. 2 and 3 includes a core material and a clad material each including a high-transmission optical glass for illumination, which is a material having a linear expansion coefficient lower than a linear expansion coefficient of a material included in each of barrels 38 and 44, which will be described later.

A distal end face of the light guide 22 is formed so as to face the illuminating light emitting section 21. On the other hand, a proximal end portion of the light guide 22 is inserted through the insertion portion 10, the operation portion 11 and the universal cable 12. Then, a proximal end face of the light guide 22 is arranged so as to be opposed to the light source section in the endoscope body 2 when the universal cable 12 is connected to the endoscope body 2.

With this configuration, illuminating light emitted from the light source section is transmitted via the light guide 22 and passes through the illuminating light emitting section 21 to be emitted toward a site to be observed.

Figure 3:
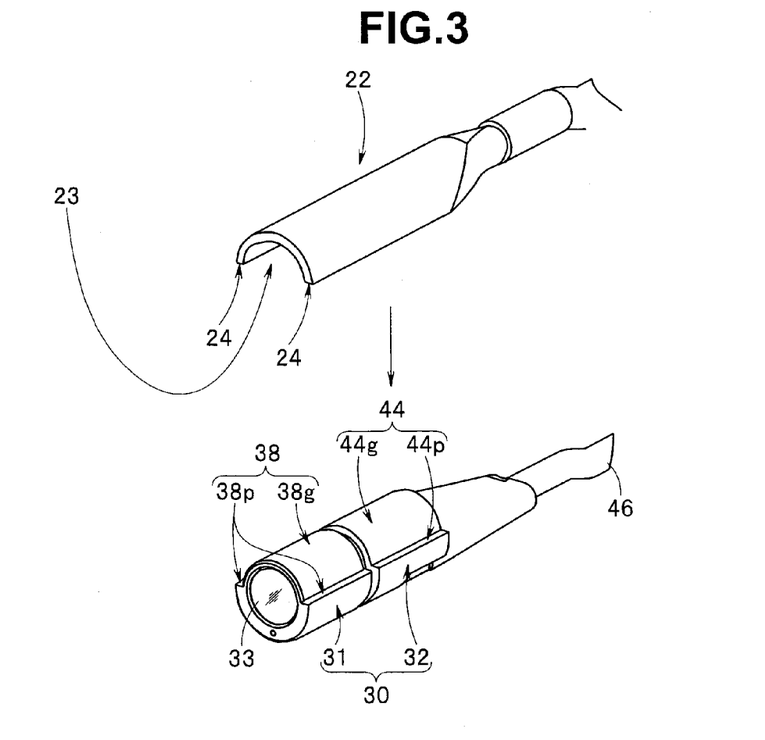
FIG. 3 is a diagram illustrating a relationship between an image pickup optical system and a light guide fiber bundle.

The image pickup optical system 30 includes an objective optical section 31 and an image pickup optical section 32, which are illustrated in FIGS. 2 and 3.

As illustrated in FIG. 2, the objective optical section 31 includes, for example, a plurality of optical lenses 33, 34, 35, 36 and 37 and a first barrel 38, which is a lens barrel. The first barrel 38 is made of, for example, stainless steel. The first barrel 38 houses the optical lenses 33, 34, 35, 36 and 37, which are integrally and fixedly provided via, e.g., bonding. The first barrel 38 is not limited to one made of stainless steel, and may be a member made of a metal such as brass (metal member).

The image pickup optical section 32 includes an image pickup apparatus 42 with a solid image pickup device 41 mounted therein, a prism 43 and a second barrel 44.

For the solid image pickup device 41, e.g., a CCD or a CMOS sensor is employed.

A plurality of signal wires 45 is connected to the proximal end side of the image pickup apparatus 42. The signal wires 45 are bundled into one signal cable 46, which is inserted through the insertion portion 10, the operation portion 11 and the universal cable 12. The plurality of signal wires 45 is electrically connected to the CPU and the electric components in the endoscope body 2 as a result of the universal cable 12 being connected to the body 2.

The prism 43 is an optical member, and forms an optical image passed through the optical lenses 33, 34, 35, 36 and 37 in the objective optical section 31, on a non-illustrated image pickup surface of the solid image pickup device 41. Reference numeral 47 denotes a positioning and securing member, which fixes the prism 43 at a predetermined position inside the barrel 44.

The second barrel 44 is made of stainless steel as with the first barrel 38. The second barrel 44 houses the prism 43, the positioning and securing member 47 and the solid image pickup device 41 therein.

The solid image pickup device 41 is fixed to a surface of the prism 43 in an integrated manner via a transparent adhesive. A part of the image pickup apparatus 42, the prism 43 and the positioning and securing member 47 are integrally fixed inside the second barrel 44 via bonding.

In other words, the linear expansion coefficient of the first barrel 38 and the linear expansion coefficient of the second barrel 44 are each higher than a linear expansion coefficient of each of the core material and the clad material included in the light guide 22.

As illustrated in FIG. 2, the second barrel 44 is arranged so as to fit over the first barrel 38. More specifically, the first barrel 38 includes a first joining portion 38r on the proximal end side. On the other hand, the second barrel 44 includes a second joining portion 44f on the distal end side.

In the present embodiment, an inner circumferential face of the second joining portion 44f is arranged on an outer circumferential face of the first joining portion 38r, whereby the first barrel 38 and the second barrel 44 are disposed in series. In this disposition state, the first barrel 38 and the second barrel 44 are slidable relative to each other in a longitudinal direction of the barrels.

Reference numeral 38p in FIG. 3 denotes each of first positioning surfaces provided at outer faces of the first barrel 38. Axial flat surfaces 24 provided at opposite side portions across a recess portion of a distal end recess portion 23 of the light guide 22 are arranged so as to be in contact with the respective first positioning surfaces 38p.

Reference numeral 44p denotes a second positioning surface provided at an outer face of the second barrel 44. The axial flat surfaces 24 of the light guide 22 are arranged so as to be also in contact with the respective second positioning surfaces 44p.

The first barrel 38 and the second barrel 44 are integrally fixed via a first adhesive 51. More specifically, the first barrel 38 and the second barrel 44 are fixed to each other via bonding after focusing adjustment is made so that an optical image passed through the optical lenses 33, 34, 35, 36 and 37 and the prism 43 is formed on the image pickup surface of the solid image pickup device 41 in a predetermined manner.

When the aforementioned bonding is performed, a worker first applies a predetermined amount of first adhesive 51 to a predetermined position in the outer circumferential face of the first joining portion 38r. Next, the worker arranges the second joining portion 44f so as to fit on the first joining portion 38r with the first adhesive 51 applied thereon.

Next, the worker makes a focusing adjustment by moving the first joining portion 38r and the second joining portion 44f in the axial direction. Subsequently, the worker holds the first joining portion 38r and the second joining portion 44f at the respective positions resulting from the focusing adjustment to cure the first adhesive 51.

As a result, an image pickup optical system 30, which is illustrated in FIG. 3, in which the first barrel 38 and the second barrel 44 are fixed to each other via bonding, namely, the objective optical section 31 and the image pickup optical section 32 are integrated is provided.

Note that during the focusing adjustment, the worker performs positioning surface adjustment work to make positions of the first positioning surface 38p and the second positioning surface 44p with respect to the axis correspond to each other.

Figure 4:
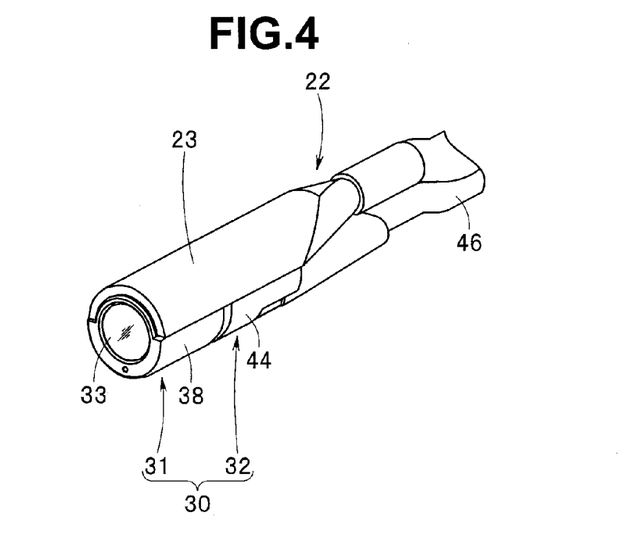
FIG. 4 is a diagram illustrating a state in which a light guide fiber bundle is bonded and fixed to an outer circumferential face of a first barrel in an objective optical section and an outer circumferential face of a second barrel in an image pickup optical section.

As illustrated in FIGS. 2 to 4, in the present embodiment, the light guide 22 is firmly fixed to the image pickup optical system 30 in an integrated manner via a second adhesive 52. More specifically, the light guide 22 includes the distal end recess portion 23 on the distal end side.

An shape of an inner face of the distal end recess portion 23 correspond to a shape of an outer circumferential face of a first light guide adhering surface 38g, which is an outer face of the first barrel 38, and a shape of an outer circumferential face of a second light guide adhering surface 44g, which is an outer face of the second barrel 44. In other words, the shape of the outer circumferential face of the first light guide adhering surface 38g and the shape of the outer circumferential face of the second light guide adhering surface 44g, which is an outer face of the second barrel 44, are the same.

The inner face of the distal end recess portion 23 of the light guide 22 is fixed to both surfaces of the first light guide adhering surface 38g of the first barrel 38 and the second light guide adhering surface 44g of the second barrel 44 via bonding.

When the above-described mentioned bonding is performed, the worker first applies a predetermined amount of second adhesive 52 to respective predetermined positions in the first light guide adhering surface 38g and the first positioning surfaces 38p of the first barrel 38 and respective predetermined positions in the second light guide adhering surface 44g and the second positioning surfaces 44p of the second barrel 44.

Next, the worker arranges the inner face of the distal end recess portion 23 of the light guide 22 and the axial flat surfaces 24 respectively on the first light guide adhering surface 38g and the first positioning surfaces 38p and the second light guide adhering surface 44g and the second positioning surfaces 44p with the second adhesive 52 applied thereon.

Subsequently, the worker holds such disposition state to cure the second adhesive 52.

As a result, as illustrated in FIG. 4, the distal end recess portion 23 of the light guide 22 is provided integrally with the image pickup optical system 30.

In the present embodiment, a bonding strength of the second adhesive 52 is set to be higher than a bonding strength of the first adhesive 51. In other words, a bonding force of the second adhesive 52 is set to be stronger than a bonding force of the first adhesive 51.

In the above description, the inner face of the distal end recess portion 23 of the light guide 22 is arranged on, e.g., the light guide adhering surfaces 38g and 44g with the second adhesive 52 applied thereon. However, it is possible that after the inner face of the distal end recess portion 23 of the light guide 22 is arranged on the light guide adhering surfaces 38g and 44g, the second adhesive 52 is applied to bond and fix the distal end recess portion 23 of the light guide 22 to the image pickup optical system 30.

In other words, the second adhesive 52 may be an adhesive having fluidity, namely, having a viscosity lower than that of the first adhesive 51.

Furthermore, where the endoscope is used under a high temperature environment, the second adhesive 52 is an adhesive having a heatproof temperature higher than that of the first adhesive 51.

Note that in FIG. 2, reference numeral 16a denotes each of a plurality of bending pieces included in the bending portion 16. Adjacent bending pieces 16a are joined in such a manner that the bending pieces 16a are pivotable with respect to an axis substantially perpendicular to a center axis of the insertion portion 10.

Reference numeral 18 denotes a bending rubber. The bending rubber 18 covers a bending portion set including the plurality of bending pieces 16a jointed to one another.

Non-illustrated bending operation wires are inserted through the bending portion 16 and the flexible tube portion 17. Distal ends of the bending operation wires are fixed to a distal end bending piece 16f included in a distal end of the bending portion set. Proximal ends of the bending operation wires are fixed to a non-illustrated bending operation mechanism provided inside the operation portion 11.

An operation of the endoscope 3 configured as described above will be described.

When the endoscope 3 is used under a high temperature environment, a temperature of the first barrel 38 in the objective optical section 31 and a temperature of the second barrel 44 included in the image pickup optical section 32, which are included in the image pickup optical system 30 incorporated in the distal end portion 15 of the insertion portion 10, each become a high temperature. On the other hand, when the endoscope 3 is transported under a low temperature environment, the temperature of the first barrel 38 and the temperature of the second barrel 44 each become a low temperature.

In the present embodiment, an expansion amount and a contraction amount of the light guide 22 axially expanded/contracted by heat are smaller than an expansion amount and a contraction amount of each of the barrels 38 and 44 axially expanded/contracted by heat. Furthermore, in the present embodiment, the first barrel 38 and the second barrel 44 are fixed to each other via the first adhesive 51. Furthermore, the barrels 38 and 44 in the image pickup optical system 30 and the distal end recess portion 23 of the light guide 22 are integrally fixed to each other via the second adhesive 52 having a bonding force stronger than that of the first adhesive 51.

In other words, the first barrel 38 and the second barrel 44 are firmly and integrally fixed to the light guide 22 that less expands/contracts depending on change in temperature, via the second adhesive 52. As a result, expansion/contraction of the first barrel 38 and the second barrel 44 depending on change in environmental temperature after focusing adjustment is inhibited by the light guide 22.

Accordingly, it is possible to prevent defocusing occurring as a result of displacement in the axial direction of the positions of the first barrel 38 and the second barrel 44 due to change in temperature.

Furthermore, as a result of the heatproof temperature of the second adhesive 52 being set to be higher than the heatproof temperature of the first adhesive 51, even in case the bonding strength of the first adhesive 51 decreases under a high temperature environment, the second adhesive 52 and the light guide 22 withstand the high temperature, enabling the positional relationship between the first barrel 38 and the second barrel 44 to be maintained.

In the above-described embodiment, the first barrel 38 and the second barrel 44 are integrated via the first adhesive 51 to form the image pickup optical system 30, and subsequently, the distal end recess portion 23 of the light guide 22 is integrally fixed to an outer face of the first barrel 38 and an outer face of the second barrel 44 via the second adhesive 52.

Figure 5:
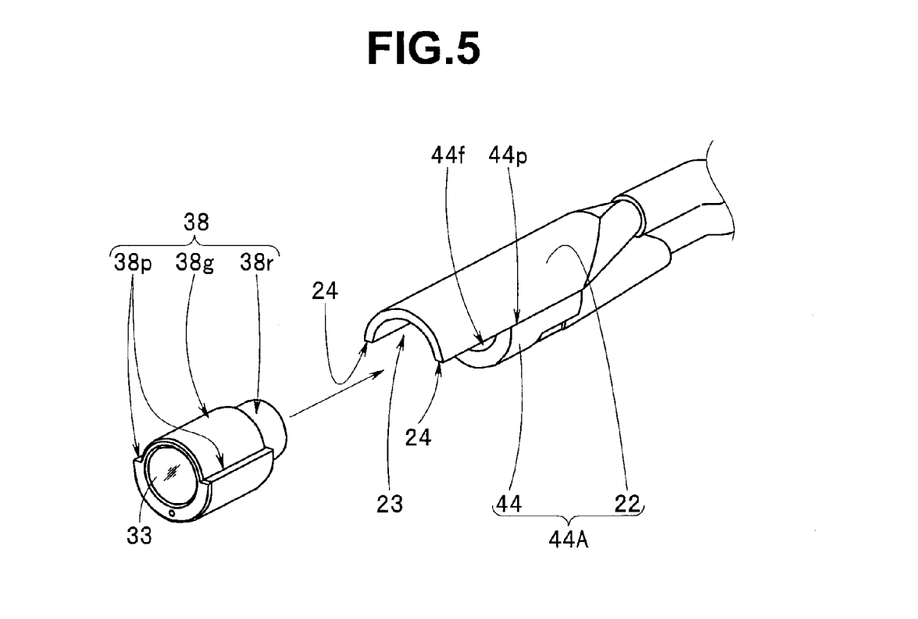
Figure 6:
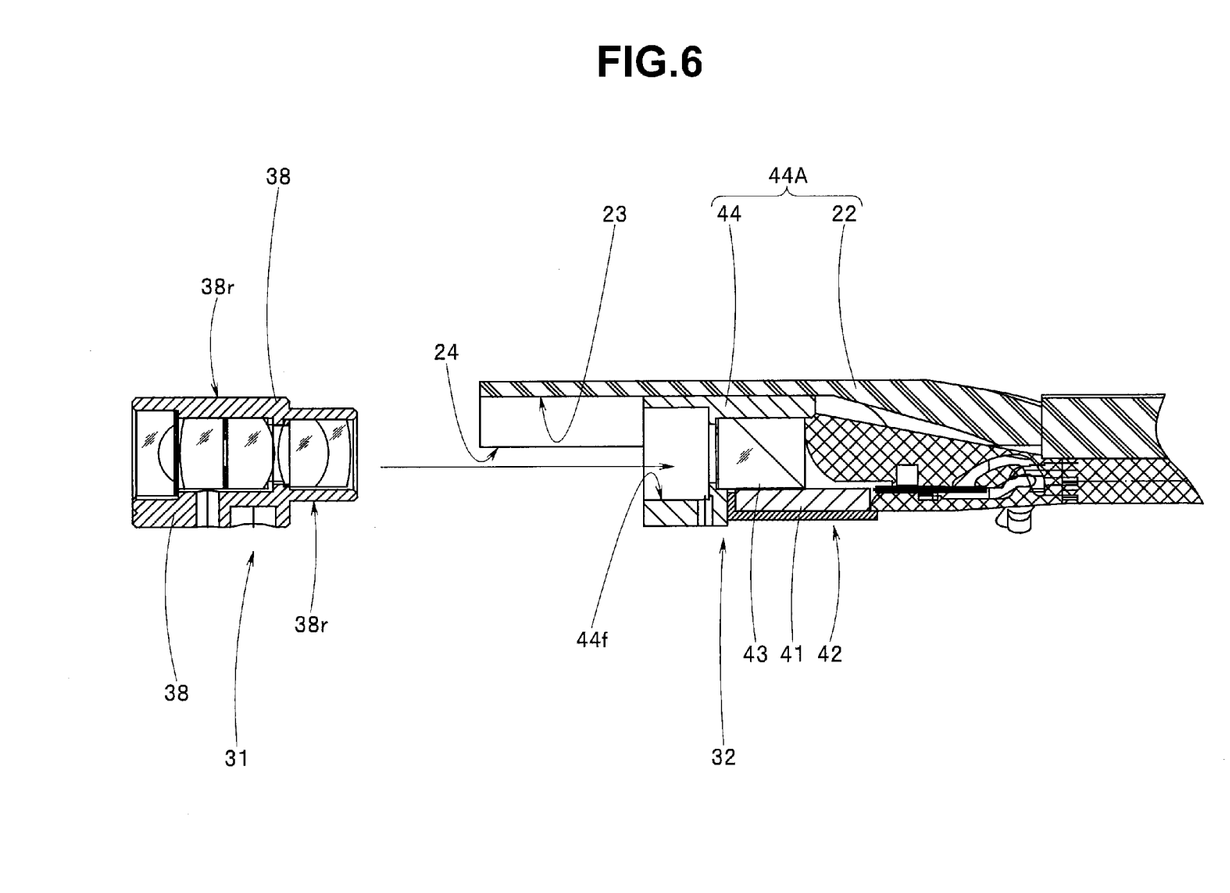
FIG. 6 is a longitudinal cross-sectional view illustrating the set of the first barrel and the second barrel.

However, the assembling procedure according to the present invention is not limited to the above-described procedure, and may be a procedure such as illustrated in FIGS. 5 and 6. In the case of this assembling procedure, for the second adhesive 52, an adhesive having a curing time period longer than a curing time period of the first adhesive 51 is used.

In the present embodiment, a worker first applies a predetermined amount of second adhesive 52 to respective predetermined positions in second light guide adhering surface 44g and second positioning surfaces 44p of a second barrel 44.

Next, as illustrated in FIG. 5, the worker arranges predetermine areas of an inner face and axial flat surfaces 24 of the distal end recess portion 23 of the light guide 22 on the second light guide adhering surface 44g and the second positioning surfaces 44p with the second adhesive 52 applied thereon.

Subsequently, the worker holds the disposition state to cure the second adhesive 52. As a result, a second barrel portion set 44A illustrated in FIGS. 5 and 6 in which the distal end recess portion 23 of the light guide 22 is integrated with the second barrel 44 is formed.

Next, the worker applies a predetermined amount of first adhesive 51 to a predetermined position in an outer circumferential face of a first joining portion 38r of a first barrel 38. Also, the worker applies a predetermined amount of second adhesive 52 to predetermined positions in a first light guide adhering surface 38g and first positioning surfaces 38p of the first barrel 38.

Next, the worker arranges the first joining portion 38r with the first adhesive 51 applied thereon so as to fit in the second joining portion 44f with the first positioning surfaces 38p of the first barrel 38 and the axial flat surfaces 24 of the distal end recess portion 23 of the light guide 22 included in the second barrel portion set 44A in contact with each other.

Next, the worker makes a focusing adjustment by moving the first barrel 38 and the second barrel portion set 44A in an axial direction. Subsequently, the worker holds the first barrel 38 and the second barrel portion set 44A at the positions resulting from the focusing adjustment to cure the first adhesive 51 as well as curing the second adhesive 52. As a result, the observation optical section 50 illustrated in FIG. 6 is formed.

As described above, after formation of the second barrel portion set 44A, the first barrel 38 is fixed to the second barrel 44 and the light guide 22 included in the second barrel portion set 44A. As a result, the need for the aforementioned positioning surface adjustment work to make positions of the first positioning surfaces 38p and the second positioning surfaces 44p with respect to the axis to be aligned is eliminated, enabling enhancement in workability of assembling the observation optical section 50.

Furthermore, as a result of an adhesive having a curing time period longer than the curing time period of the first adhesive 51 being used for the second adhesive 52, a focusing adjustment can be made with plenty of time.

Figure 7:
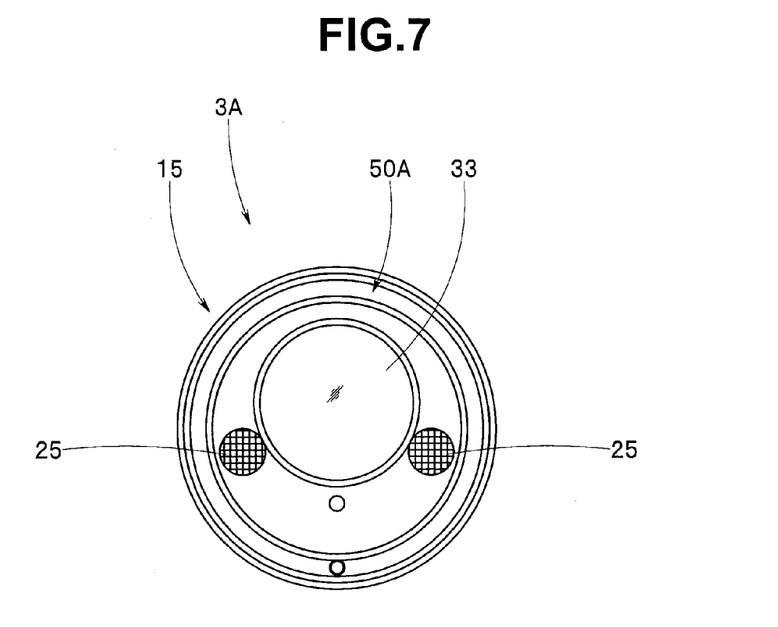
FIG. 7 is a front view illustrating a distal end portion of the endoscope, the endoscope including a light emitting device as an illumination optical system.
Figure 8:
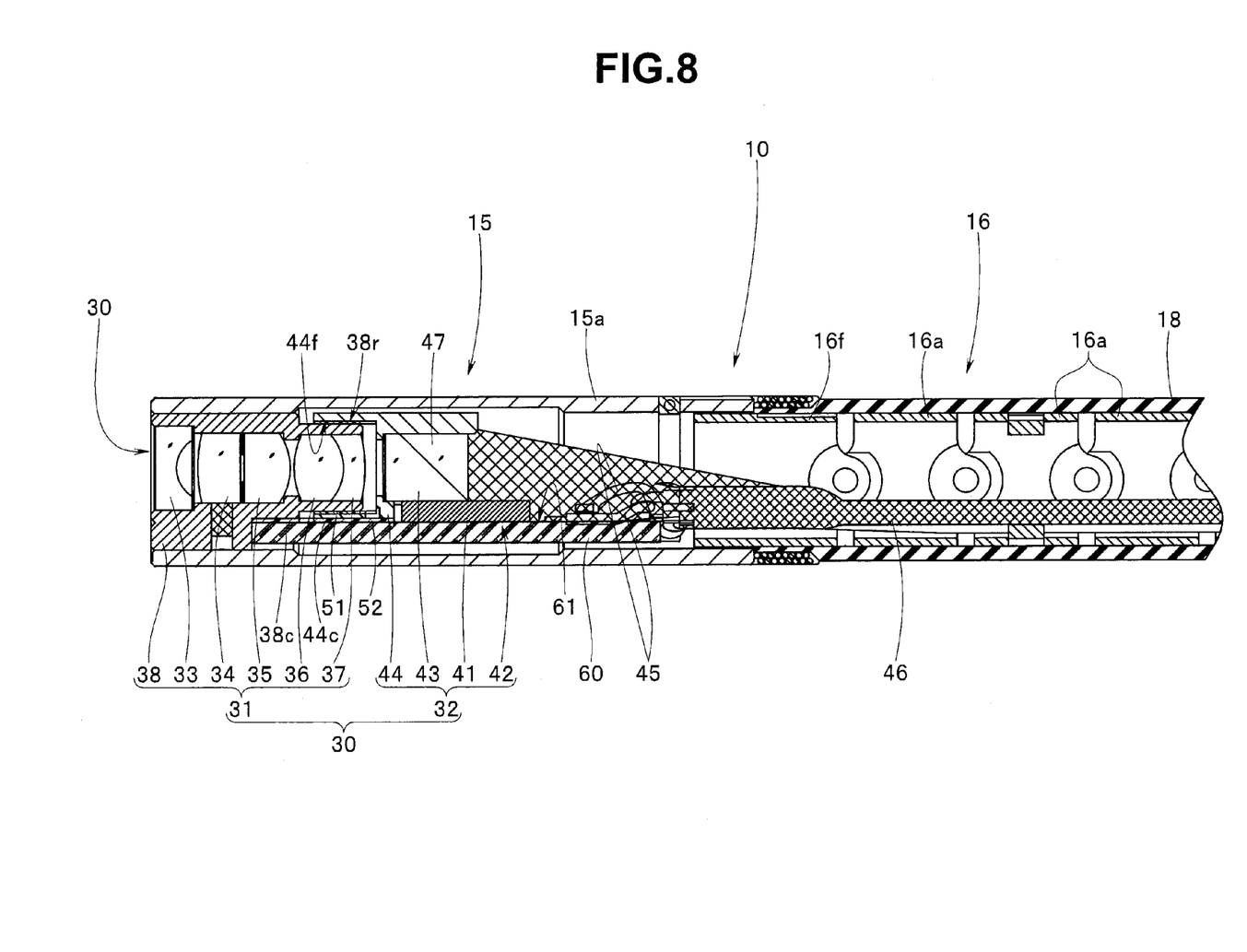
FIG. 8 is a longitudinal cross-sectional view illustrating a configuration of a distal end portion of the endoscope, the endoscope including a light emitting device as an illumination optical system.

In the above-described embodiments, the light guide 22 is used for the illumination optical system 20. In addition, the above-described embodiments have the configuration in which the inner face of the distal end recess portion 23 of the light guide 22 is bonded and fixed to the first light guide adhering surface 38g of the first barrel 38 and also to the second light guide adhering surface 44g of the second barrel 44. However, a through hole in the axial direction may be formed in the first barrel 38 and a distal end portion of the light guide, which corresponds to the shape of the through hole, may be arranged in the through hole. In this configuration, the second adhesive 52 is applied to the inner surface of the through hole and the distal end portion of the light guide 22 is bonded and fixed to the inner surface of the through hole. However, the illumination optical system according to the present invention is not limited to a light guide, and as illustrated in FIGS. 7 and 8, a configuration in which, for example, light emitting devices 25 such as LEDs may be provided at a distal end portion 15 of an endoscope 3A. In other words, in the present embodiment, an illumination optical system 20A is formed by the light emitting devices 25.

In this configuration, a first barrel 38 and a second barrel 44 are integrally fixed to a three-dimensional circuit substrate 60 via a second adhesive 52. The three-dimensional circuit substrate 60 is a holding member and is made of ceramic, which is a material having a linear expansion coefficient lower than a linear expansion coefficient of each of the first barrel 38 and the second barrel 44. The three-dimensional circuit substrate 60 is formed so as to have, for example, an axially-elongated flat rectangular parallelepiped shape.

More specifically, in the present embodiment, the first barrel 38 and the second barrel 44 are arranged on a surface 61, which is a flat surface of the three-dimensional circuit substrate 60. Thus, the first barrel 38 is provided with a first close-contact surface 38c to be arranged so as to be in close contact with the surface 61 of the three-dimensional circuit substrate 60, and the second barrel 44 is provided with a second close-contact surface 44c to be arranged so as to be in close contact with the surface 61 of the three-dimensional circuit substrate 60.

Also, the solid image pickup device 41 is arranged on the surface 61 side of the three-dimensional circuit substrate 60. Furthermore, pads (not illustrated) for electrical connection of signal wires 45 are provided on the surface 61 side of the three-dimensional circuit substrate 60.

The rest of configuration is similar to those of the above-described embodiments, and members that are the same as those of the above-described embodiments are provided with reference numerals that are the same as those of the above-described embodiments, and a description thereof will be omitted.

With this configuration, as with the above-described embodiments, the first barrel 38 and the second barrel 44 are firmly and integrally fixed to the three-dimensional circuit substrate 60 that less expands/contracts depending on change in temperature, via the second adhesive 52.

As a result, it is possible to prevent defocusing occurring as a result of displacement in the axial direction of the positions of the first barrel 38 and the second barrel 44 due to change in temperature.

In the above-described embodiments, the second barrel is a member made of a metal (metal member). However, a part of the second barrel, the part fitting with the first barrel, may include, for example, a transparent resin, which is a material that transmits light.

With this configuration, as a result of an adhesive that is cured by ultraviolet light being used for a first adhesive, an accuracy of fixation of the first barrel and the second barrel to each other can be set to be high.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
    an objective optical section including a plurality of optical lenses, and a first barrel that houses the optical lenses, the optical lenses being integrally and fixedly provided therein;
    an image pickup optical section including a solid image pickup device, an optical member that forms an optical image passed through the objective optical section on an image pickup surface of the solid image pickup device, and a second barrel that houses the optical member and the solid image pickup device, the optical member and the solid image pickup device being integrally and fixedly provided therein, the second barrel being arranged so as to fit with the first barrel, and being fixed to the first barrel in an integrated manner via bonding after adjustment in position in an axial direction relative to the first barrel;
    a holding member including a material having a linear expansion coefficient lower than a linear expansion coefficient of the first barrel and a linear expansion coefficient of the second barrel, the holding member being fixed to a predetermined position on an outer surface of the first barrel and a predetermined position on an outer surface of the second barrel via bonding;
    a first adhesive that bonds the first barrel and the second barrel to each other; and
    a second adhesive having a bonding strength higher than the bonding strength of the first adhesive, the second adhesive bonding the holding member to the outer surface of the first barrel or an inner surface of a through hole of the first barrel, and to the outer surface of the second barrel.

2. The endoscope according to claim 1,
    wherein each of the first barrel and the second barrel comprise a metal member; and
    wherein the holding member is a light guide fiber bundle included in an illumination optical system, the light guide fiber bundle having a linear expansion coefficient lower than the linear expansion coefficients of the metal member included in each of the first and second barrels.

3. The endoscope according to claim 2, wherein the metal member in each of the first and second barrels is stainless steel or brass.

4. The endoscope according to claim 1, wherein
    each of the first barrel and the second barrel comprise a metal member, and
    the holding member is made of a ceramic having a linear expansion coefficient lower than the linear expansion coefficient of the metal member included in each of the first and second barrels.

5. The endoscope according to claim 4, wherein the holding member made of the ceramic is a three-dimensional circuit substrate and is electrically connected to the solid image pickup device.

6. The endoscope according to claim 1, wherein a heatproof temperature of the second adhesive is higher than a heatproof temperature of the first adhesive.

7. The endoscope according to claim 1, wherein a viscosity of the second adhesive is equivalent to or lower than a viscosity of the first adhesive.

8. The endoscope according to claim 1, wherein a curing time period of the first adhesive is shorter than a curing time period of the second adhesive.

9. The endoscope according to claim 2,
    wherein the light guide fiber bundle includes a distal end recess portion and an axial flat surface; and
    wherein the first barrel and the second barrel each include a light guide adhering surface on which an inner face of the distal end recess portion is arranged and a positioning surface on which the axial flat surface is arranged.

10. The endoscope according to claim 5,
    wherein the three-dimensional circuit substrate includes a flat surface to which the solid image pickup device is electrically connected; and
    wherein the first barrel and the second barrel each include a close-contact surface on which the three-dimensional circuit substrate is arranged in close contact.

11. The endoscope according to claim 1,
    wherein at least a part of the second barrel, the part fitting with the first barrel, includes a material that transmits light; and
    wherein the first adhesive is an adhesive that is cured by ultraviolet light.

* * * * *